US011413106B2

(12) United States Patent
Purpura

(10) Patent No.: US 11,413,106 B2
(45) Date of Patent: Aug. 16, 2022

(54) CATHETER STORAGE ASSEMBLY

(71) Applicant: Gerald Purpura, Ocala, FL (US)

(72) Inventor: Gerald Purpura, Ocala, FL (US)

( * ) Notice: Subject to any disclaimer, the term of this patent is extended or adjusted under 35 U.S.C. 154(b) by 238 days.

(21) Appl. No.: 16/866,669

(22) Filed: May 5, 2020

(65) Prior Publication Data

US 2021/0346111 A1 Nov. 11, 2021

(51) Int. Cl.
*A61B 50/31* (2016.01)
*A45C 5/03* (2006.01)
*A45C 13/02* (2006.01)
*A45C 9/00* (2006.01)

(52) U.S. Cl.
CPC ............... *A61B 50/31* (2016.02); *A45C 5/03* (2013.01); *A45C 9/00* (2013.01); *A45C 13/02* (2013.01); *A45C 2200/15* (2013.01); *A61B 2050/311* (2016.02)

(58) Field of Classification Search
CPC ..... A61B 50/31; A61B 2050/311; A45C 5/03; A45C 9/00; A45C 13/02
USPC ....... 206/570, 207, 210, 223, 571, 576, 371, 206/364
See application file for complete search history.

(56) References Cited

U.S. PATENT DOCUMENTS

| | | | | |
|---|---|---|---|---|
| 1,625,547 A | * | 4/1927 | Kessler | A61F 17/00 211/70.1 |
| 4,429,793 A | * | 2/1984 | Ehmann | A61M 5/003 62/457.2 |
| 4,522,302 A | | 6/1985 | Paikoff | |
| 4,934,549 A | * | 6/1990 | Allen | A45C 11/20 220/520 |
| D398,772 S | | 9/1998 | Benham | |
| 5,799,791 A | * | 9/1998 | Harley | A45C 9/00 206/757 |
| 5,979,658 A | | 11/1999 | Allen | |
| 6,640,976 B1 | | 11/2003 | Franks-Farah | |
| 6,740,068 B1 | | 5/2004 | Aruffo | |
| 8,397,647 B1 | * | 3/2013 | Riegel | A61M 16/021 108/26 |
| 2004/0118477 A1 | | 6/2004 | Desmond | |
| 2007/0084742 A1 | * | 4/2007 | Miller | A61B 50/20 206/438 |
| 2007/0199958 A1 | * | 8/2007 | Barraclough | A47J 45/065 222/465.1 |
| 2008/0249482 A1 | | 10/2008 | Erez | |
| 2010/0059560 A1 | * | 3/2010 | Lanum | A61B 50/31 224/257 |

(Continued)

FOREIGN PATENT DOCUMENTS

KR 20070091985 A * 9/2007
WO WO2007120256 10/2007

*Primary Examiner* — Rafael A Ortiz

(57) ABSTRACT

A catheter storage assembly includes a case that is positionable in an open position such that the case forms a table. The case has a first half that is hingedly coupled to a second half. A plurality of pockets is each coupled to the case and each of the pockets has an open end for receiving objects commonly employed for catheterization. A plurality of first legs and a plurality of second legs are each pivotally coupled to the case. Each of the first legs and the second legs is positionable in a deployed position to support the case above a support surface when the case is opened to form the table. A plurality of closures is each coupled to the first half of the case for retaining the case in a closed position.

10 Claims, 7 Drawing Sheets

(56) References Cited

U.S. PATENT DOCUMENTS

2018/0338602 A1* 11/2018 Marrero ................ A45D 40/20

* cited by examiner

CATHETER STORAGE ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to storage devices and more particularly pertains to a new storage device for transporting objects for performing self catheterization.

(2) Description of Related Art Including Information Disclosed Under 37 CFR 1.97 and 1.98.

The prior art relates to storage devices including a medical kit than contains a plurality of medical devices which are contained in sterile packaging. The prior art discloses a storage box that has a plurality of rectilinear storage compartments being integrated therein and a lid that includes securing flaps. The prior art also discloses a self-catheterization kit that includes all of the necessary tools for performing a self-catheterization. The prior art also discloses a post-operational care kit that includes medical equipment to facilitate a patient to care for a post-surgical drain site. Additionally, the prior art discloses a re-usable squeeze tube for storing viscous fluids.

BRIEF SUMMARY OF THE INVENTION

An embodiment of the disclosure meets the needs presented above by generally comprising a case that is positionable in an open position such that the case forms a table. The case has a first half that is hingedly coupled to a second half. A plurality of pockets is each coupled to the case and each of the pockets has an open end for receiving objects commonly employed for catheterization. A plurality of first legs and a plurality of second legs are each pivotally coupled to the case. Each of the first legs and the second legs is positionable in a deployed position to support the case above a support surface when the case is opened to form the table. A plurality of closures is each coupled to the first half of the case for retaining the case in a closed position.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
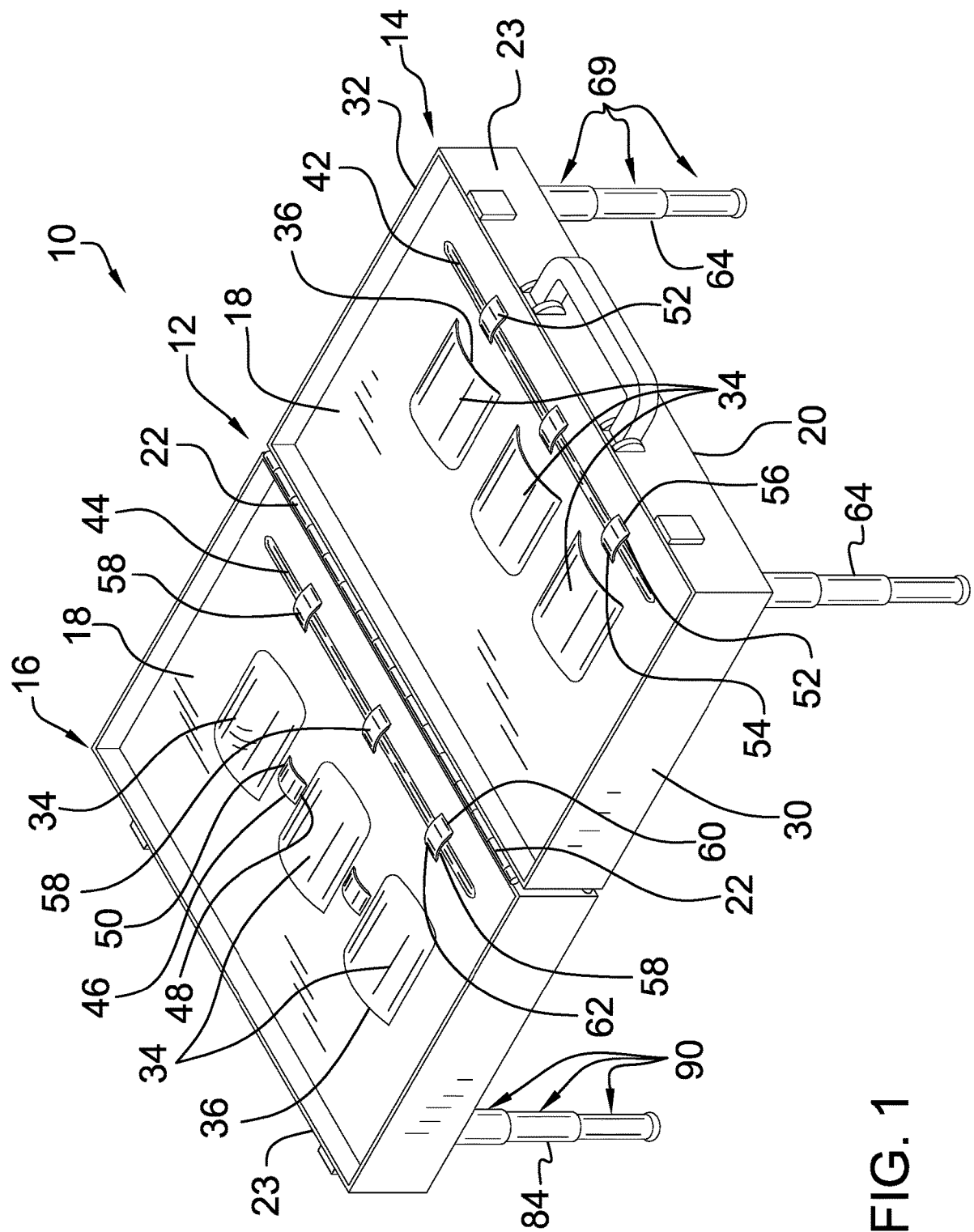
FIG. 1 is a top perspective view of a catheter storage assembly according to an embodiment of the disclosure.
Figure 2:
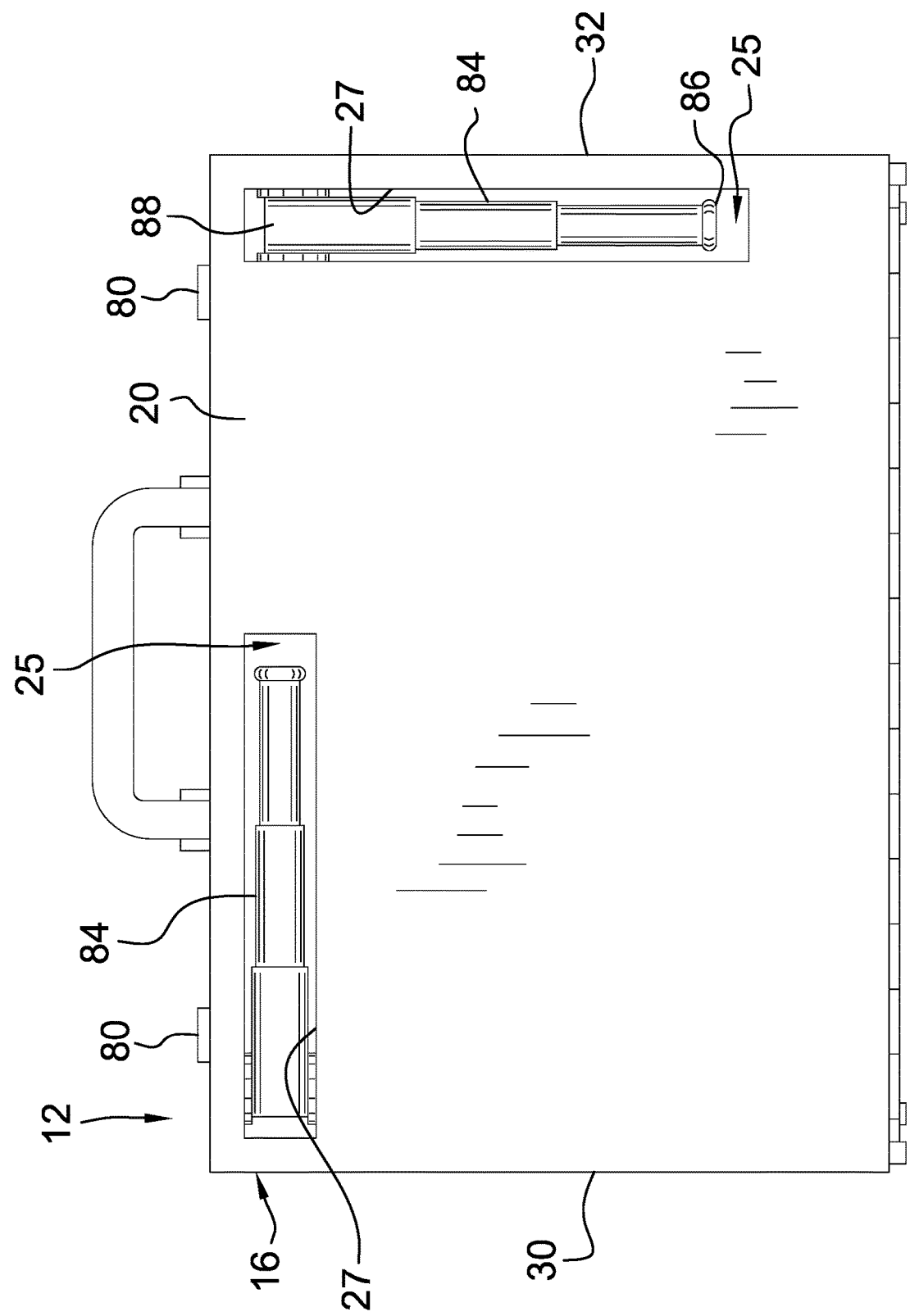
FIG. 2 is a top view of an embodiment of the disclosure.
Figure 3:
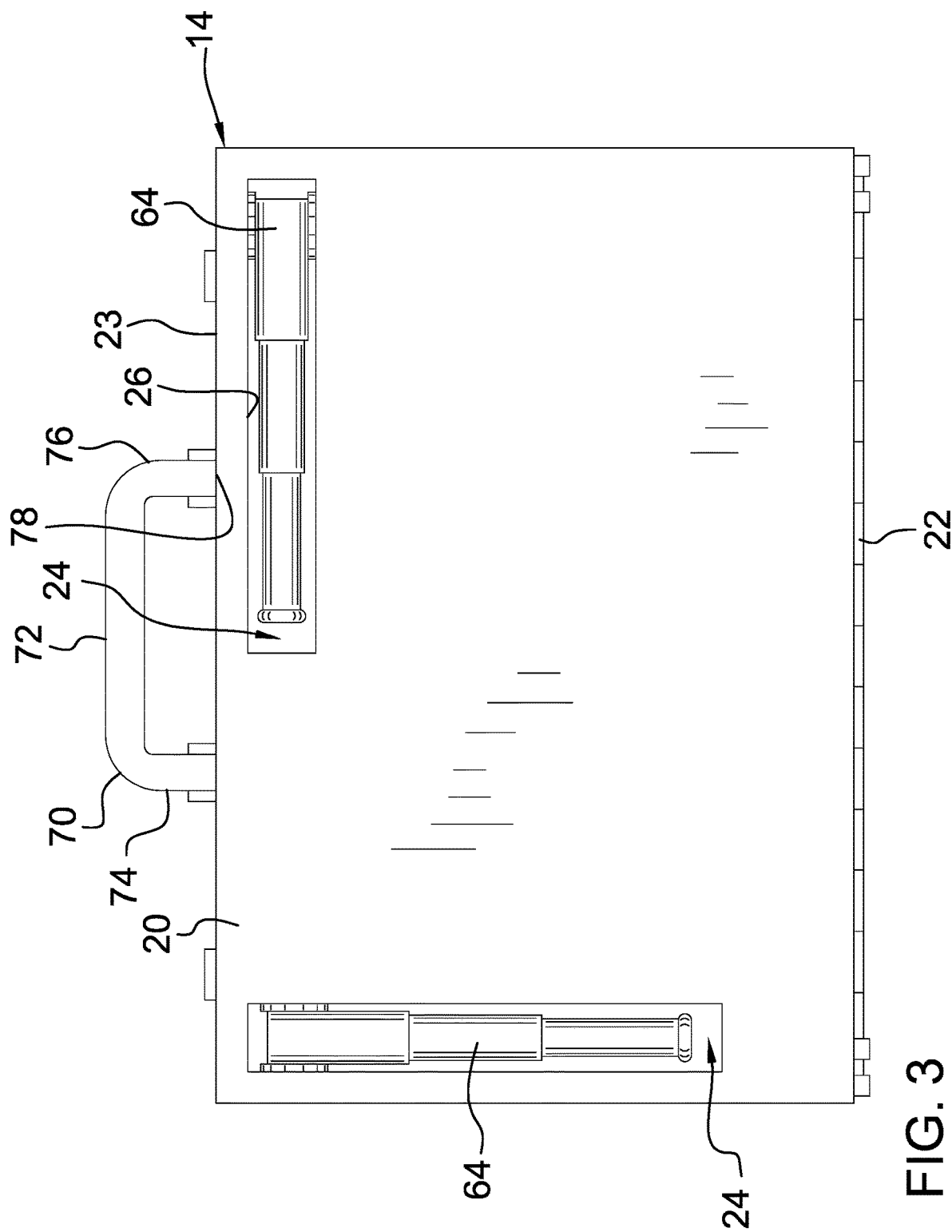
FIG. 3 is a bottom view of an embodiment of the disclosure.
Figure 5:
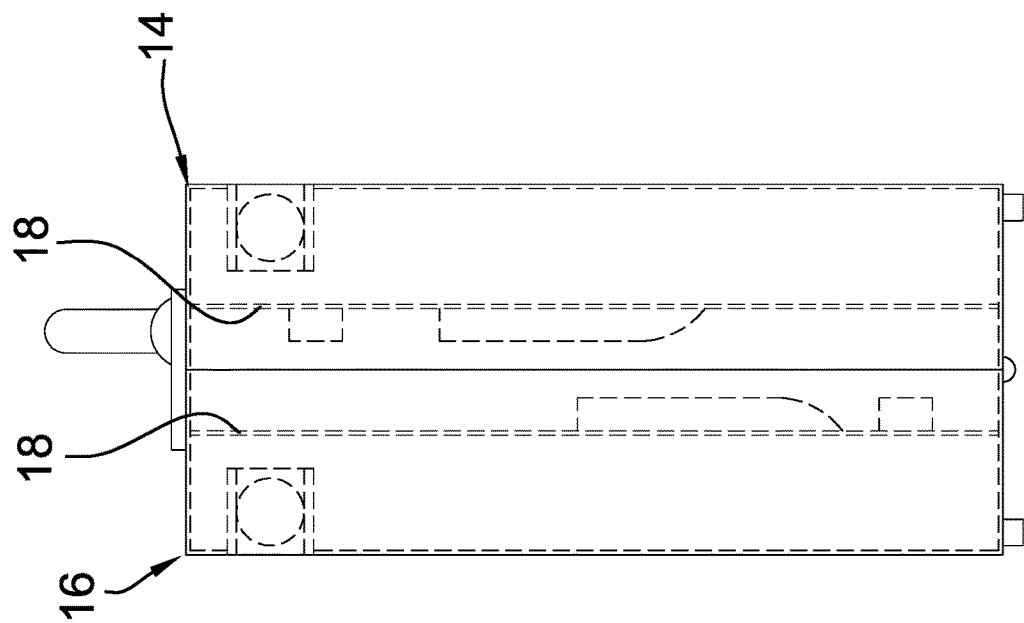
FIG. 5 is a left side phantom view of an embodiment of the disclosure.
Figure 4:
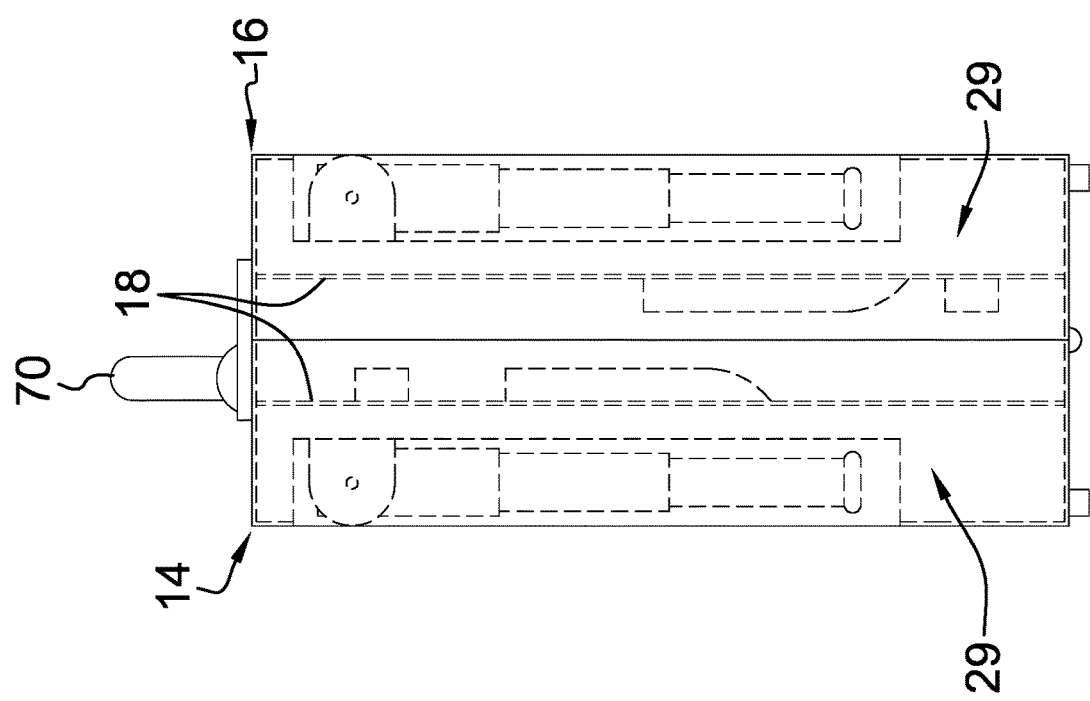
FIG. 4 is a right side phantom view of an embodiment of the disclosure.
Figure 6:
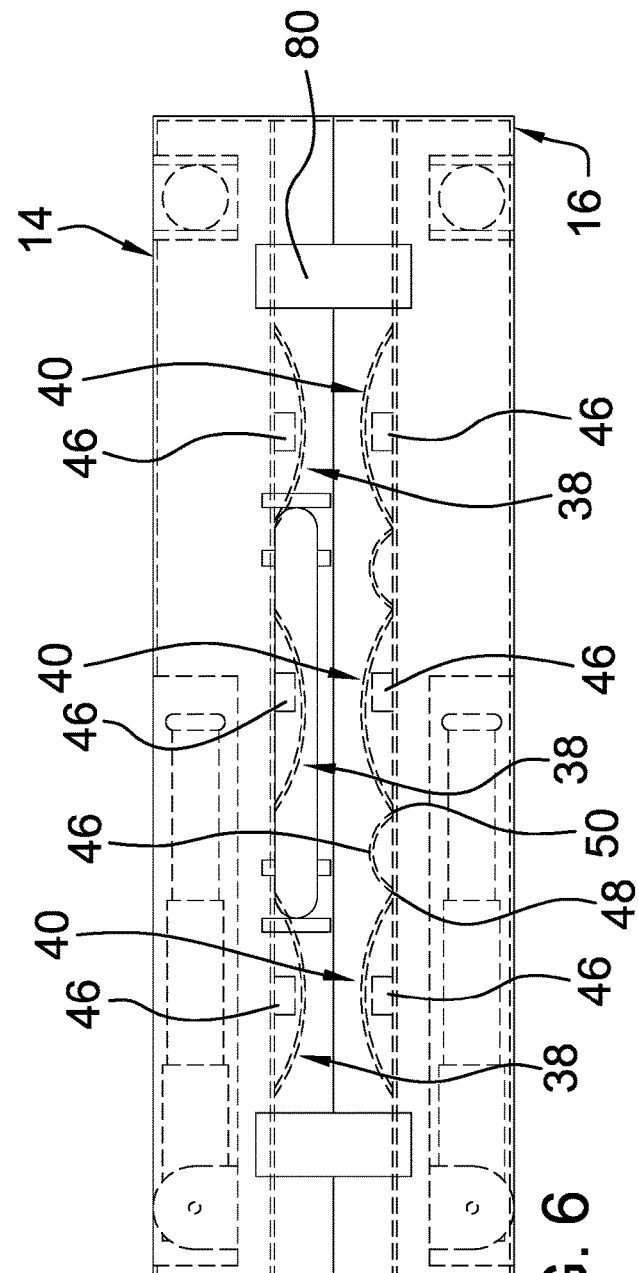
FIG. 6 is a top phantom view of an embodiment of the disclosure.
Figure 7:
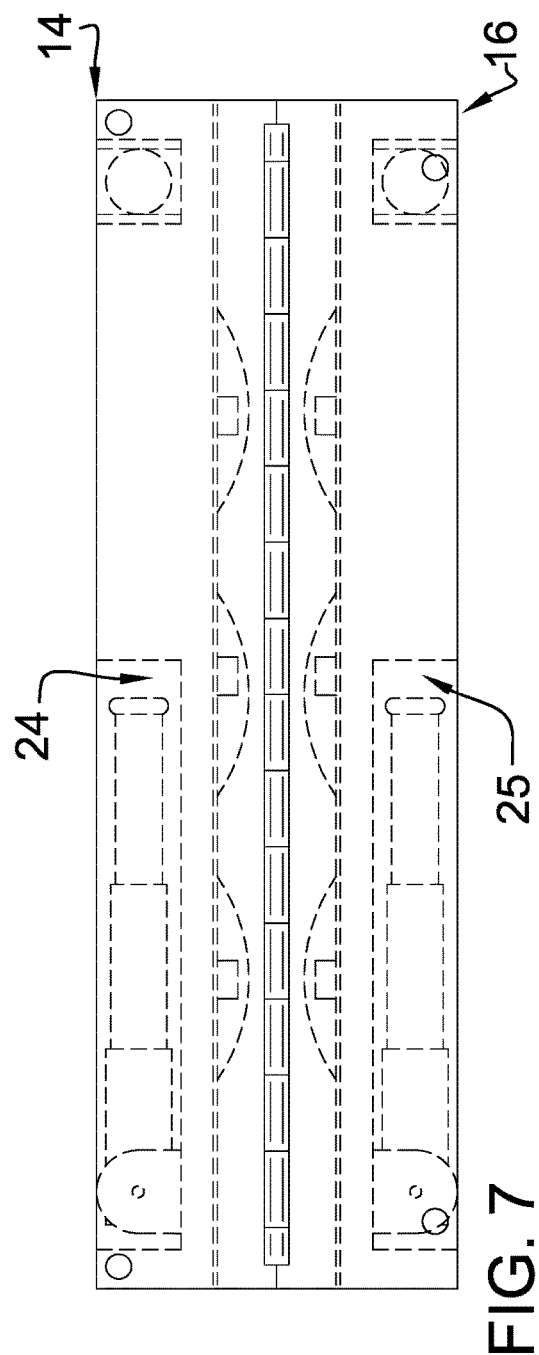
FIG. 7 is a bottom phantom view of an embodiment of the disclosure.
Figure 8:
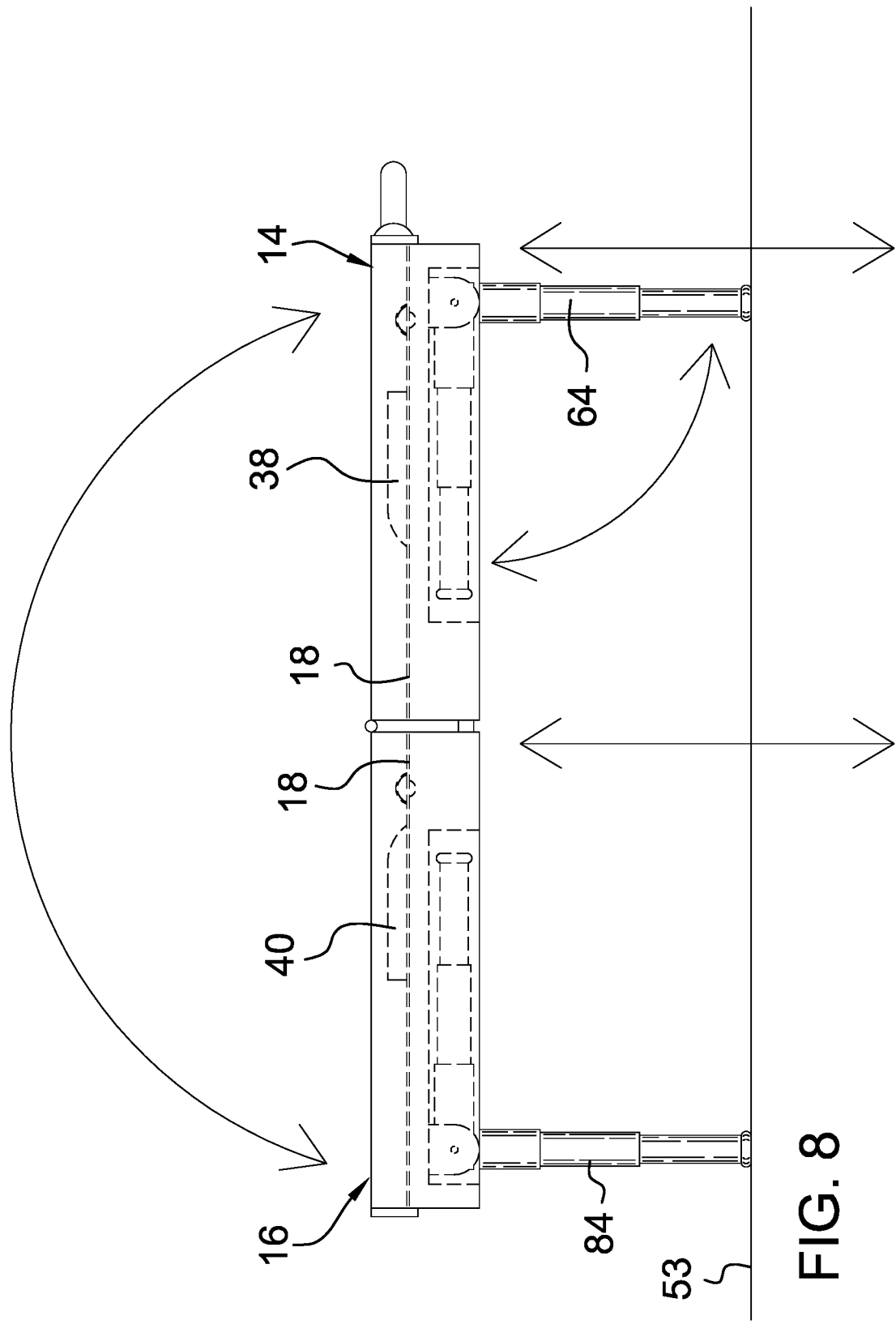
FIG. 8 is a phantom view of an embodiment of the disclosure showing a case being positioned in an open position.
Figure 9:
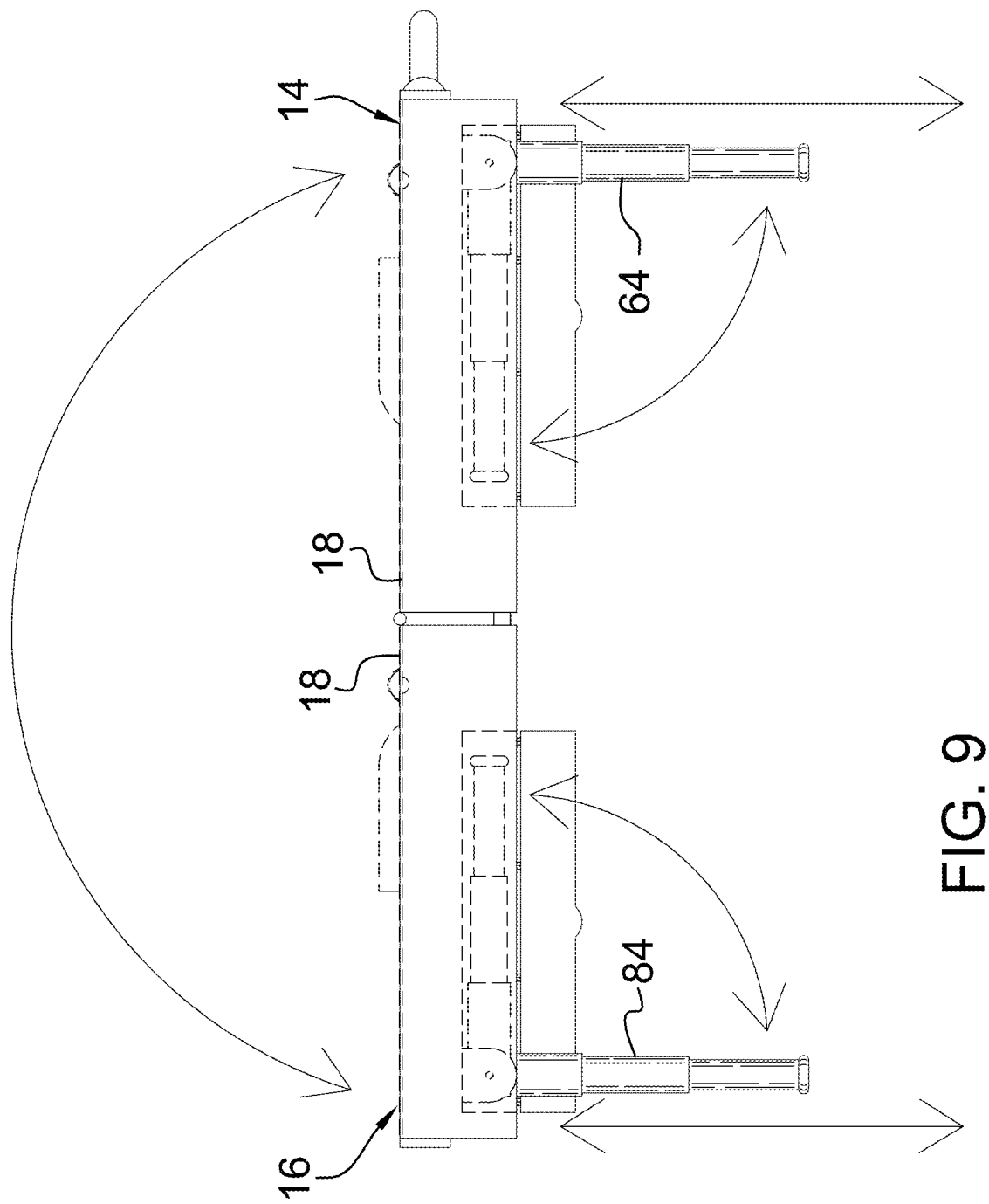
FIG. 9 is a phantom view of an alternative embodiment of the disclosure.

With reference now to the drawings, and in particular to FIGS. 1 through 9 thereof, a new storage device embodying the principles and concepts of an embodiment of the disclosure and generally designated by the reference numeral 10 will be described.

As best illustrated in FIGS. 1 through 9, the catheter storage assembly 10 generally comprises a case 12 that is positionable in an open position such that the case 12 forms a table. The case 12 has a first half 14 that is hingedly coupled to a second half 16. Each of the first half 14 and the second half 16 has a top side 18, a bottom side 20, a first lateral side 22 and a second lateral side 23. The first lateral side 22 of the first half 14 is hingedly coupled to the first lateral side 22 of the second half 16. The top side 18 of the first half 14 faces the top side 18 of the second half 16 when the case 12 is in a closed position. Conversely, the top side 18 of each of the first half 14 and the second half 16 lies on a plane that is coplanar with each other when the case 12 is positioned in an open position such that the case 12 forms the table.

The top side 18 of each of the first half 14 and the second half 16 may comprise a removable panel that defines a storage area 29 within each of the first half 14 and the second half 16. The bottom side 20 of the first half 14 has a plurality of first wells 24 each extending toward the top side 18 of the first half 14. Each of the first wells 24 is elongated and each of the first wells 24 has a bounding surface 26. The plurality of first wells 24 is oriented collinear with a respective one of the first lateral side 22 and a back side 32 of the first half 14. The bottom side 20 of the second half 16 has a plurality of second wells 25 each extending toward the top side 18 of the second half 16. Each of the second wells 25 is elongated and each of the second wells 25 has a bounding surface 27. The plurality of second wells 25 is oriented collinear with a respective one of the second lateral side 23 and a front side 30 of the second half 16.

A plurality of pockets 34 is provided and each of the pockets 34 is coupled to the case 12. Each of the pockets 34 has an open end 36 for receiving objects commonly employed for catheterization thereby facilitating the case 12 to transport the objects. The objects may include, but not be limited to, alcohol wipes, catheter lubricant, vinyl gloves, waste bags or other objects commonly used to facilitate the process of self catheterization. Each of the pockets 34 may be comprised of a translucent material thereby facilitating contents of the pockets 34 to be visible. The plurality of pockets 34 includes a set of first pockets 38 and a set of second pockets 40. Each of the first pockets 38 is positioned on the top side 18 of the first half 14 and each of the second pockets 40 is positioned on the top side 18 of the second half 16.

A first groove 42 extends downwardly into the top side 18 of the first half 14 for storing a catheter. A second groove 44 extends downwardly into the top side 18 of the second half 16 for storing a catheter. Each of the first catheter and the second catheter may be a catheter of any conventional design that is employed for human catheterization. A plurality of loops 46 is each coupled to the case 12 to have an object positioned therebeneath for storage. Each of the loops 46 is positioned on the top side 18 of the second half 16 of the case 12.

Each of the loops 46 has a first end 48 and a second end 50, and the first end 48 and the second end 50 of each of the loops 46 is coupled to the top side 18 of the second half 16. Each of the loops 46 is positioned between a respective pair of the second pockets 40. Each of the loops 46 is comprised of a resiliently stretchable material to retain the object therebeneath. The objects stored beneath the loops 46 may include a bottle of hand sanitizer, a pair of scissors or other tools commonly employed during a self catheterization process.

A plurality of first straps 52 is each coupled to the first half 14 of the case 12 and each of the first straps 52 has a fixed end 54 with respect to the top side 18 of the first half 14. Each of the first straps 52 has a free end 56 with respect to the top side 18 of the first half 14 and each of the first straps 52 extends across the first groove 42. The free end 56 of each of the first straps 52 is matable to the top side 18 of the first half 14 to retain the catheter in the first groove 42. The plurality of first straps 52 is spaced apart from each other and is distributed along the full length of the first groove 42.

A plurality of second straps 58 is each coupled to the second half 16 of the case 12 and each of the second straps 58 has a fixed end 60 with respect to the top side 18 of the second half 16. Each of the second straps 58 has a free end 62 with respect to the top side 18 of the second half 16, and each of the second straps 58 extends across the second groove 44. The free end 62 of each of the second straps 58 is matable to the top side 18 of the second half 16 to retain the catheter in the second groove 44.

A plurality of first legs 64 is provided and each of the first legs 64 is pivotally coupled to the first half 14 of the case 12. Each of the first legs 64 is positionable in a stored position having each of the first legs 64 resting against the first half 14. Each of the first legs 64 is positionable in a deployed position having each of the first legs 64 being oriented perpendicular to the first half 14. In this way each of the first legs 64 can support the case 12 above a support surface 52 when the case 12 is opened to form the table. The support surface 52 may be a floor or other horizontal support surface.

Each of the first legs 64 has a first end 66 and a second end 68, and each of the first legs 64 comprises a plurality of sections 66 that slidably engage each other such that each of the first legs 64 has a telescopically adjustable length. The first end 66 of each of the first legs 64 is pivotally coupled to the bounding surface 26 of a respective one of the first wells 24 in the bottom side 20 of the first half 14. Each of the first legs 64 is stored within the respective well when the first legs 64 are positioned in the stored position. Conversely, each of the first legs 64 is oriented perpendicular to the bottom side 20 of the first half 14 when the first legs 64 are positioned in the deployed position.

A handle 70 is movably coupled to the case 12 for carrying the case 12, and the handle 70 has a central section 72 extending between a first section 74 and a second section 76. A distal end 78 of each of the first section 74 and the second section 76 is pivotally coupled to the second lateral side 23 of the first half 14 of the case 12 to facilitate the central section 72 to be gripped. A plurality of closures 80 is provided and each of the closures 80 is coupled to the first half 14 of the case 12. Each of the closures 80 releasably engages the second half 16 of the case 12 when the case 12 is positioned in the closed position for retaining the case 12 in the closed position.

A plurality of second legs 84 is each pivotally coupled to the second half 16 of the case 12. Each of the second legs 84 is positionable in a stored position having each of the second legs 84 resting against the second half 16. Additionally, each of the second legs 84 is positionable in a deployed position having each of the second legs 84 being oriented perpendicular to the second half 16. In this way the second legs 84 can support the case 12 above the support surface 52 when the case 12 is opened to form the table.

Each of the second legs 84 has a first end 86 and a second end 88, and each of the second legs 84 comprises a plurality of sections 90 that slidably engage each other such that each of the second legs 84 has a telescopically adjustable length. The second end 88 of each of the second legs 84 is pivotally coupled to the bounding surface 27 of a respective one of the second wells 25 in the bottom side 20 of the second half 16. Each of the second legs 84 is stored within the respective second well 25 when the second legs 84 are positioned in the stored position. Conversely, each of the second legs 84 is oriented perpendicular to the bottom side 20 of the second half 16 when the second legs 84 are positioned in the deployed position. As is most clearly shown in FIGS. 1 through 8, the top side 18 of the first half 14 and the second half 16 of the case 12 may be recessed. As is most clearly shown in FIG. 9, the top side 18 of the first half 14 and the second half 16 may not be recessed.

In use, all of the attendant objects related to performing self catheterization is stored within the case 12. The case 12 is carried into the handicapped stall of a bathroom, for example, when a user needs to perform self catheterization. Each of the first legs 64 is positioned in the deployed position, the case 12 is stoop upon the support surface 52 and the case 12 is opened. In this way all of the objects are available to the user to facilitate the user to safely and cleanly perform the self catheterization. Additionally, the case 12 facilitates the user to discretely transport the objects for self catheterization thereby enhancing peace of mind for the user.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A catheter storage assembly for storing items employed during self catheterization, said assembly comprising:
    a case being positionable in an open position such that said case forms a table, said case having a first half being hingedly coupled to a second half, wherein each of said first half and said second half has a top side, a bottom side, a first lateral side and a second lateral side, said first lateral side of said first half being hingedly coupled to said first lateral side of said second half, said top side of said first half facing said top side of said second half when said case is in a closed position, said top side of each of said first half and said second half lying on a plane being coplanar with each other when said case is positioned in an open position such that said case forms said table;
    a plurality of pockets, each of said pockets being coupled to said case, each of said pockets having an open end for receiving objects commonly employed for catheterization wherein said case is configured to transport the objects;
    a first groove extending downwardly into said top side of said first half wherein said first groove is configured to store a catheter;
    a second groove extending downwardly into said top side of said second half wherein said second groove is configured to store a catheter;
    a plurality of loops, each of said loops being coupled to said case wherein each of said loops is configured to have an object positioned therebeneath for storage;
    a plurality of first legs, each of said first legs being pivotally coupled to said first half of said case, each of said first legs being positionable in a stored position having each of said first legs resting against said first half, each of said first legs being positionable in a deployed position having each of said first legs being oriented perpendicular to said first half wherein each of said first legs is configured to support said case above a support surface when said case is opened to form said table;
    a plurality of second legs, each of said second legs being pivotally coupled to said second half of said case, each of said second legs being positionable in a stored position having each of said second legs resting against said second half, each of said second legs being positionable in a deployed position having each of said second legs being oriented perpendicular to said second half wherein each of said second legs is configured to support said case above a support surface when said case is opened to form said table;
    a handle being movably coupled to said case for carrying said case;
    a plurality of closures, each of said closures being coupled to said first half of said case, each of said closures releasably engaging said second half of said case when said case is positioned in said closed position for retaining said case in said closed position; and
    a plurality of first straps, each of said first straps being coupled to said first half of said case, each of said first straps having a fixed end with respect to said top side of said first half, each of said first straps having a free end with respect to said top side of said first half, each of said first straps extending across said first groove, said free end of each of said first straps being matable to said top side of said first half wherein each of said first straps is configured to retain the catheter in said first groove.

2. The assembly according to claim 1, wherein said bottom side of said first half has a plurality of first wells each extending toward said top side of said first half, each of said first wells being elongated, each of said first wells having a bounding surface, said plurality of first wells being oriented collinear with a respective one of said first lateral side, a second lateral side, a front side and a back side of said first half.

3. The assembly according to claim 2, further comprising said bottom side of said second half has a plurality of second wells each extending toward said top side of said second half, each of said second wells being elongated, each of said second wells having a bounding surface, said plurality of second wells being oriented collinear with a respective one of said second lateral side and said front side of said second half.

4. The assembly according to claim 1, wherein said plurality of pockets includes a set of first pockets and a set of second pockets, each of said first pockets being positioned on said top side of said first half, each of said second pockets being positioned on said top side of said second half.

5. The assembly according to claim 1, wherein each of said loops is positioned on said top side of said second half of said case, each of said loops having a first end and a second end, said first end and said second end of each of said loops being coupled to said top side of said second half, each of said loops being positioned between a respective pair of said second pockets, each of said loops being comprised of a resiliently stretchable material wherein each of said loops is configured to retain the object therebeneath.

6. The assembly according to claim 1, further comprising a plurality of second straps, each of said second straps being coupled to said second half of said case, each of said second straps having a fixed end with respect to said top side of said second half, each of said second straps having a free end with respect to said top side of said second half, each of said second straps extending across said second groove, said free end of each of said second straps being matable to said top side of said second half wherein each of said second straps is configured to retain the catheter in said second groove.

7. The assembly according to claim 2, wherein each of said first legs has a first end and a second end, each of said first legs comprising a plurality of sections that slidably engage each other such that each of said first legs has a telescopically adjustable length, said first end of each of said first legs being pivotally coupled to said bounding surface of a respective one of said first wells in said bottom side of said first half, each of said first legs being stored within said respective well when said first legs are positioned in said stored position, each of said first legs being oriented perpendicular to said bottom side of said first half when said first legs are positioned in said deployed position.

8. The assembly according to claim 3, wherein each of said second legs has a first end and a second end, each of said second legs comprising a plurality of sections that slidably engage each other such that each of said second legs has a telescopically adjustable length, said second end of each of said second legs being pivotally coupled to said bounding surface of a respective one of said second wells in said bottom side of said second half, each of said second legs being stored within said respective second well when said second legs are positioned in said stored position, each of said second legs being oriented perpendicular to said bottom side of said second half when said second legs are positioned in said deployed position.

9. The assembly according to claim 2, wherein said handle has a central section extending between a first section and a second section, a distal end of each of said first section and said second section being pivotally coupled to said second lateral side of said first half of said case wherein said central section is configured to be gripped.

10. A catheter storage assembly for storing items employed during self catheterization, said assembly comprising:
    a case that is positionable in an open position such that said case forms a table, said case having a first half being hingedly coupled to a second half, each of said first half and said second half having a top side, a bottom side, a first lateral side and a second lateral side, said first lateral side of said first half being hingedly coupled to said first lateral side of said second half, said top side of said first half facing said top side of said second half when said case is in a closed position, said top side of each of said first half and said second half lying on a plane being coplanar with each other when said case is positioned in an open position such that said case forms said table, said bottom side of said first half having a plurality of first wells each extending toward said top side of said first half, each of said first wells being elongated, each of said first wells having a bounding surface, said plurality of first wells being oriented collinear with a respective one of said first lateral side and said back side of said first half, said bottom side of said second half having a plurality of second wells each extending toward said top side of said second half, each of said second wells being elongated, each of said second wells having a bounding surface, said plurality of second wells being oriented collinear with a respective one of said second lateral side and said front side of said second half;
    a plurality of pockets, each of said pockets being coupled to said case, each of said pockets having an open end for receiving objects commonly employed for catheterization wherein said case is configured to transport the objects, said plurality of pockets including a set of first pockets and a set of second pockets, each of said first pockets being positioned on said top side of said first half, each of said second pockets being positioned on said top side of said second half;
    a first groove extending downwardly into said top side of said first half wherein said first groove is configured to store a catheter;
    a second groove extending downwardly into said top side of said second half wherein said second groove is configured to store a catheter;
    a plurality of loops, each of said loops being coupled to said case wherein each of said loops is configured to have an object positioned therebeneath for storage, each of said loops being positioned on said top side of said second half of said case, each of said loops having a first end and a second end, said first end and said second end of each of said loops being coupled to said top side of said second half, each of said loops being positioned between a respective pair of said second pockets, each of said loops being comprised of a resiliently stretchable material wherein each of said loops is configured to retain the object therebeneath;
    a plurality of first straps, each of said first straps being coupled to said first half of said case, each of said first straps having a fixed end with respect to said top side of said first half, each of said first straps having a free end with respect to said top side of said first half, each of said first straps extending across said first groove, said free end of each of said first straps being matable to said top side of said first half wherein each of said first straps is configured to retain the catheter in said first groove;
    a plurality of second straps, each of said second straps being coupled to said second half of said case, each of said second straps having a fixed end with respect to said top side of said second half, each of said second straps having a free end with respect to said top side of said second half, each of said second straps extending across said second groove, said free end of each of said second straps being matable to said top side of said second half wherein each of said second straps is configured to retain the catheter in said second groove;
    a plurality of first legs, each of said first legs being pivotally coupled to said first half of said case, each of said first legs being positionable in a stored position having each of said first legs resting against said first half, each of said first legs being positionable in a deployed position having each of said first legs being oriented perpendicular to said first half wherein each of said first legs is configured to support said case above a support surface when said case is opened to form said table, each of said first legs having a first end and a second end, each of said first legs comprising a plurality of sections that slidably engage each other such that each of said first legs has a telescopically adjustable length, said first end of each of said first legs being pivotally coupled to said bounding surface of a respective one of said first wells in said bottom side of said first half, each of said first legs being stored within said respective first well when said first legs are positioned in said stored position, each of said first legs being oriented perpendicular to said bottom side of said first half when said first legs are positioned in said deployed position;
    a plurality of second legs, each of said second legs being pivotally coupled to said second half of said case, each of said second legs being positionable in a stored position having each of said second legs resting against said second half, each of said second legs being positionable in a deployed position having each of said second legs being oriented perpendicular to said second half wherein each of said second legs is configured to support said case above a support surface when said case is opened to form said table, each of said second legs having a first end and a second end, each of said second legs comprising a plurality of sections that slidably engage each other such that each of said second legs has a telescopically adjustable length, said second end of each of said second legs being pivotally coupled to said bounding surface of a respective one of said second wells in said bottom side of said second half, each of said second legs being stored within said respective second well when said second legs are positioned in said stored position, each of said second legs being oriented perpendicular to said bottom side of said second half when said second legs are positioned in said deployed position;

a handle being movably coupled to said case for carrying said case, said handle having a central section extending between a first section and a second section, a distal end of each of said first section and said second section being pivotally coupled to said second lateral side of said first half of said case wherein said central section is configured to be gripped; and a plurality of closures, each of said closures being coupled to said first half of said case, each of said closures releasably engaging said second half of said case when said case is positioned in said closed position for retaining said case in said closed position.

\* \* \* \* \*